(12) United States Patent
Framroze

(10) Patent No.: US 9,446,013 B2
(45) Date of Patent: Sep. 20, 2016

(54) METHOD OF LOWERING CIRCULATING OXIDIZED LOW DENSITY LIPOPROTEIN-BETA-2-GLYCOPROTEIN 1 COMPLEX FOR TREATMENT OF ATHEROSCLEROSIS

(76) Inventor: Bomi Patel Framroze, Mumbai (IN)

( * ) Notice: Subject to any disclaimer, the term of this patent is extended or adjusted under 35 U.S.C. 154(b) by 596 days.

(21) Appl. No.: 13/125,806

(22) PCT Filed: Nov. 10, 2009

(86) PCT No.: PCT/IB2009/007669
§ 371 (c)(1),
(2), (4) Date: Apr. 23, 2011

(87) PCT Pub. No.: WO2010/055419
PCT Pub. Date: May 20, 2010

(65) Prior Publication Data
US 2011/0207821 A1    Aug. 25, 2011

Related U.S. Application Data

(60) Provisional application No. 61/114,823, filed on Nov. 14, 2008.

(51) Int. Cl.
*A61K 31/202* (2006.01)
*A61K 31/20* (2006.01)
*A23L 1/30* (2006.01)
*A61K 9/48* (2006.01)
*A61K 31/201* (2006.01)

(52) U.S. Cl.
CPC .............. *A61K 31/20* (2013.01); *A23L 1/3006* (2013.01); *A61K 9/4858* (2013.01); *A61K 31/201* (2013.01); *A61K 31/202* (2013.01)

(58) Field of Classification Search
CPC combination set(s) only.
See application file for complete search history.

(56) References Cited

U.S. PATENT DOCUMENTS 4,826,877 A * 5/1989 Stewart .................. A61K 31/16
514/549

FOREIGN PATENT DOCUMENTS

EP            1964554 A1 * 9/2008
WO   WO 2008085019 A1 * 7/2008

OTHER PUBLICATIONS

Tatarczyk et al., "Analysis of long-chain ω-3 fatty acid content in fish-oil supplements," Wien Klin Wochenschr, Jul. 2007, vol. 119; No. 13-14: 417-422.*
Lopez et al., "Oxidized low-density lipoprotein and β2-glycoprotein I in patients with systemic lupus erythematosus and increased carotid intima-media thickness: implications in autoimmune-mediated atherosclerosis," Lupus, Feb. 2006, vol. 15, No. 2, 80-86—abstract only.*
Takeshita et al., "Myeloperoxidase Generates 5-Chlorouracil in Human Atherosclerotic Tissue: A Potential Pathway for Somatic Mutagenesis by Macrophages," Journal of Biol. Chem., Feb. 2006, vol. 281, No. 6, pp. 3906-3104.*
International Search Report for PCT/IB2009/007669.
International Search Opinion for PCT/IB2009/007669.

* cited by examiner

*Primary Examiner* — Karl J Puttlitz
(74) *Attorney, Agent, or Firm* — Altimatia, LLC; David M. Gange

(57) ABSTRACT

Embodiments of the invention comprise methods of reducing circulating oxidized low density lipoprotein-beta-2-glycoprotein 1 and circulating Myeloperoxidase levels by administering to subjects an effective amount of a dietary oil composition containing 20-90 wt % polyunsaturated fatty acids. Lowering oxidized low density lipoprotein-beta-2-glycoprotein complex and Myeloperoxidase levels may be an effective treatment of atherosclerosis.

7 Claims, No Drawings

METHOD OF LOWERING CIRCULATING OXIDIZED LOW DENSITY LIPOPROTEIN-BETA-2-GLYCOPROTEIN 1 COMPLEX FOR TREATMENT OF ATHEROSCLEROSIS

CROSS REFERENCE TO RELATED APPLICATIONS

This application claims the benefit of U.S. Provisional Application for Patent No. 61/114,823 filed on Nov. 14, 2008.

FIELD

Embodiments of the invention relate to natural poly unsaturated fatty acid (PUFA) containing cooking oil compositions that lower circulating oxidized low density lipoprotein-beta-2-glycoprotein 1 complex for prevention and treatment of atherosclerosis.

BACKGROUND

Elevated circulatory cholesterol is an established risk factor in the development of atherosclerosis. Atherosclerosis can be described as the process of the weakening of arterial walls and a narrowing of the blood flow within these vessels. This sequence of events frequently occurs in the coronary arteries, causing blockage of blood flow to the heart and leading to myocardial infarction (heart damage); it is often termed coronary heart disease (CHD).

Therapeutic agents, such as statins, which control the concentration of serum cholesterol, have shown some effectiveness in the treatment of coronary heart disease. These agents modulate circulating levels of cholesterol-carrying, lipoproteins by inhibiting cholesterol synthesis itself, but have no effect on downstream events such as cholesterol absorption or oxidation, which are necessary steps for initiating atherosclerosis. However, cholesterol levels are constantly under upward pressure due to high dietary intake of animal fat, and on account of the body's synthesis of cholesterol in the liver and other tissue when dietary supply is deemed inadequate.

Four major classes of lipoproteins are known, all of which share a similar basic structure of a lipid nucleus surrounded by an amphiphilic surface layer of phospholipids and apolipoproteins. The larger the lipid nucleus the less dense is the lipoprotein particle. In increasing order of size they are: high density lipoprotein (HDL), which develops a lipid core by scavenging cholesterol from peripheral tissue and hence is often referred to as "good cholesterol"; low density lipoprotein (LDL), which forms in the liver from very low density lipoprotein (VLDL) remnants; very low density lipoproteins (VLDL), which are also made in the liver and contain mostly triglycerides and chylomicrons which are formed in the small intestine and are made up of triglycerides and dietary fat.

A number of patents disclose compounds which are useful anti-atherosclerotic agents. For example, U.S. Pat. No. 4,681,893, which discloses a "Method of Inhibiting cholesterol biosynthesis in a patient," and U.S. Pat. No. 5,846,966, which discloses "Combinations of hydroxy-substituted azetidinone compounds and HMG CoA Reductase Inhibitors," This patent (U.S. Pat. No. 4,681,893) and all other patents and patent applications mentioned in the present application are hereby incorporated herein by reference.

More recent evidence supports the belief that LDL needs to undergo a series of transformations and complexation prior to the onset of atherosclerosis. A putative early step is the formation of oxidized LDL (oxLDL), which plays a pivotal role in the onset of atherosclerosis. Oxidative modification of LDL alters its biological properties, resulting in chemotaxis of monocytes or T lymphocytes in addition to the modulation of growth factors and cytokine production from endothelial cells, smooth muscle cells, and macrophages. The cytotoxicity oxLDL from cultured endothelial cells has been clearly demonstrated to be atherogenic. These studies clearly showed the atherogenic mechanisms of oxidation of LDL in arterial walls but later studies have begun to put more emphasis on the clinical importance of circulating oxLDL levels in patients with coronary heart disease. This circulating oxLDL is measured with an immunoassay using murine monoclonal antibodies prepared against malondialdehyde-modified LDL (MDA-LDL) and against copper oxLDL.

More recent trials have also shown the presence of increased plasma levels oxLDL in patients with coronary heart disease. Elevated plasma oxLDL levels have been established as a biochemical risk marker for CHD. The absence of association of oxLDL levels with other risk factors, such as hypertension, hyperlipidemia, or smoking suggests that raised oxLDL levels are an independent risk factor for CHD and when compared with other biochemical markers, such as total cholesterol, triglycerides, apoB, or HDL levels, the association between oxLDL, levels and CHD is a markedly superior risk indicator for CHD.

The uptake of oxLDL by endothelial cells has also been shown to be a critical step for the initiation and development of atherosclerosis. Adhesion molecules are inflammatory markers, which are up-regulated by oxLDL and play a pivotal role in atherogenesis. Another manner in which oxLDL may be shown to contribute to CHD is by assisting in the accumulation of apoptotic cells in atherosclerotic plaques.

Fish oil and more specifically the Eicosa Pentaenoic Acid (EPA), Docosa Pentaenoic Acid (DPA), and Docosa Hexaenoic Acid (DHA) polyunsaturated fatty acid (PUFA) constituents of fish oil have been shown to have potential use as a cardiotonic stimulant. Some in-vitro studies carried out in human coronary endothelial cells have suggested that EPA and DHA may attenuate expression of adhesion molecules which may be one pathway for an anti-atherosclerotic effect of fish and fish oils.

In another instance, the influence of dietary fish oil on aortic thrombosis, platelet aggregation, and superoxide dismutase (SOD) activity in a rat model has been studied and shown to delay formation of arterial thrombus, probably by reducing platelet aggregation and oxidative stress-associated arterial injury.

It is also well established in mono-phasic chemical systems that the highly unsaturated EPA and DHA should oxidize more readily than fatty acids that contain fewer double bonds. Previous studies have showed that enrichment of LDL, which has discrete polar and non-polar phases, with these fatty acids did not increase oxidation.

Studies by Wander (Lipids, Vol. 37, No. 8, pg 789, (2002)) have also shown that the extent of apoptosis induced by EPA/DHA-rich oxLDL compared to that induced by EPA/DHA-non-rich oxLDL in U937 cells is significantly lower thus leading to the conclusion that after PUFA supplementation, EPA/DHA-rich oxLDL-induced cell apoptosis decreased and the decrease was not related to the concentration of lipid hydroperoxides. This result suggests that EPA/DHA provides for a protective effect for atherosclerosis via a lessening of cell apoptosis in the arterial wall, rather than any reduction in oxidative damage.

Atherosclerosis has also been characterized by a gradual thickening of arterial walls due to the excessive accumulation of lipids. Pro-inflammatory factors and dyslipidemia are the main contributors to its development as described by Steinberg D., J. Biol. Chem. Vol. 272(34), pg. 20963, (1997) and Steinberg D., Nature Med. Vol. 8, pg. 1211, (2002). Low density lipoprotein (LDL) is the principal form of cholesterol that accumulates in atherosclerotic lesions or plaques, but LDL must be first modified into an oxidized structure (oxLDL) to begin the process, and as shown by McMurray H. et al. J. Clinical. Med. Vol. 92, pg. 1004, (1993) the most significant pro-atherogenic mechanism for modifying LDL into oxLDL is oxidative stress.

Unlike native LDL, oxLDL binds to $\beta_2$GPI-glycoprotein to eventually form a stable non-dissociable complex. (oxLDL-$\beta_2$GPI complex, oxidized low density lipoprotein-beta-2-glycoprotein 1 complex) These stable complexes are regarded as pathogenic and highly clinically relevant and have been implicated as pro-atherogenic antigens and represent a serologic risk factor to the development of atherothrombosis.

The Role of MPO

Myeloperoxidase (MPO) is a heme peroxidase-cyclooxygenase enzyme expressed in neutrophils, monocytes and macrophages. MPO participates in the innate immune defence system by forming microbicidal reactive oxidants such as hypochlorous acid, a potent antimicrobial agent. However, hypochlorous acid has also been reported to react with nucleobases resulting in the formation of 5-chlorouracil, a marker for DNA damage during inflammation, which is enriched in human atherosclerotic tissue.

Recently evidence has emerged that MPO-derived oxidants contribute to tissue damage and the initiation and propagation of acute and chronic vascular inflammatory disease. Circulating levels of MPO have been shown to predict risks for major adverse cardiac events and specific levels of MPO-derived chlorinated compounds are known biomarkers for atherosclerosis disease progression. (Takeshita J, Byun Nhan T Q, Pritchard D K, Pennathur S, Schwartz S M et al. (2006). Myeloperoxidase generates 5-chlorouracil in human atherosclerotic tissue: a potential pathway for somatic mutagenesis by macrophages, J. Biol. Chem., 281: 3096-3104)

Another indicator for MPO-catalysed oxidation of lipid proteins is observed by hydrochlorous acid attack and formation of 3-chlorotyrosine which has been identified in human atherosclerotic lesions and lipoproteins extracted from these lesions (Hazen S L, Heinecke J W, 3-Chlorotyrosine, a specific marker of myeloperoxidase-catalyzed oxidation, is markedly elevated in low density lipoprotein isolated from human atherosclerotic intima. J Clin Invest 99: 2075-2081 (1997); Thuktani. A K, McHowat J, Hsu F F, Brennan M L, Hazen S L, Ford D A, Identification of alpha-chloro fatty aldehydes and unsaturated lysophosphatidylcholine molecular species in human atherosclerotic lesions. Circulation 108: 3128-3133 (2003)).

Surprisingly, the present inventors have found that patients using a cooking oil formulation, containing fish and/or algal oil rich in mixed PUFA's, in their daily diet, over a sustained period, showed a significant reduction in circulatory oxLDL-$\beta_2$GPI complex. The positive effect of the cooking oil formulation cannot be derived from the known and described literature.

Further surprisingly, the present inventors followed up this unexpected result with a second trial using a once-a-day dose of fish oil capsule containing a mixture of PUFA's and showed the same surprising lowering of circulatory oxLDL-$\beta_2$GPI complex levels as observed in the cooking oil trial. In a further extension of this result, the present inventors carried out a comparative trial between an oil containing predominantly a single PUFA (DHA) and an oil containing a mixture of PUFA's (DHA, EPA, DPA) and showed the surprising statistically significant additional lowering of OxLDL-$\beta_2$GPI complex levels for the mixed PUFA's as compared to oil containing predominantly a single PUFA.

In a fourth trial, the present inventors discovered a surprising, statistically significant, lowering of circulatory MPO levels for patients taking an oral dose of mixed PUFA's as compared to an untreated control group.

SUMMARY

Embodiments of the present invention comprise a novel method to reduce circulatory oxLDL-$\beta_2$GPI complex and Myeloperoxidase (MPO) by providing a daily therapeutically-effective dose of at least one of Eicosa Pentaenoic Acid (EPA), Docosa Pentaenoic Acid (DPA), and Docosa Hexaenoic Acid (DHA) polyunsaturated fatty acids (PUFA) formulated into a cooking oil composition wherein at least one of EPA, DPA, and DHA is added as a constituent of fish and/or algal oil and mixed with one or more known cooking oils such as groundnut oil, rice-bran oil, soybean oil, corn oil, sesame oil, canola oil, safflower oil, live oil, peanut oil and/or other vegetable oils it to a stable cooking oil composition.

An embodiment of the present invention comprises a method to deliver a daily therapeutically-effective dose of at least one of Eicosa Pentaenoic Acid (EPA), Docosa Pentaenoic Acid (DPA), and Docosa Hexaenoic Acid (DHA) polyunsaturated fatty acids (PUFA) by providing a daily capsule of fish and or algal oil to the patient to lower circulatory OxLDL and MPO.

DETAILED DESCRIPTION

Atherosclerosis is characterized, by a gradual thickening of arterial walls due to the excessive accumulation of lipids. Pro-inflammatory factors and dyslipidemia are the main contributors to its development. Low density lipoprotein (LDL) is the principal form of cholesterol that accumulates in atherosclerotic lesions or plaques, but LDL must be first modified into an oxidized structure (oxLDL) to begin the process, and the most significant pro-atherogenic mechanism for modifying LDL into oxLDL is oxidative stress.

Unlike native LDL, oxLDL binds to β2-glycoprotein 1 to eventually form a stable non-dissociable complex (oxLDL-$\beta_2$GPI complex). The initial reaction is reversible but is followed by the formation of stable non-dissociable complexes which are regarded (Moue K. et al., Oxidized LDL/-$\beta_2$GPI complexes. New aspects in atherosclerosis. *Lupus* 14, 736 (2005)) as pathogenic and highly clinically relevant. The uptake of oxLDL by macrophages is mediated by a scavenger receptor CD36 which leads to the formation of foam cells with atherosclerotic plaque. (Podrez E A. et al., Macrophage scavenger receptor CD36 is the major receptor for LDL modified by monocyte-generated reactive nitrogen species. *J. Clin. Invest.* 105(8), 1085 (2000)).

Since the uptake of oxLDL-$\beta_2$GPI is significantly enhanced in the presence of anti-$\beta_2$GPI antibodies, this mechanism becomes physiologically relevant in explaining the development of foam cells within the atherosclerotic plaque. Thus oxLDL-β₂GPI complexes have been implicated as pro-atherogenic antigens and represent a serologic risk factor and contributor to the development of athero-thrombosis.

Thus lowering circulating oxLDL-β₂GPI complex is a significant pharmacological target for the treatment of athero-thrombosis and is the object of the present invention.

Circulatory oxLDL-β₂GPI complex can be accurately measured using an immunometric assay based on a double-antibody 'sandwich' technique (ELISA) that detects the circulating oxLDL-β₂GPI complex in human plasma. The wells of a 96-well plate are coated with a monoclonal antibody against human β₂GPI which will bind any β₂GPI introduced into the well. Bound oxLDL-β₂GPI is detected using a horseradish peroxidase (HRP)-labeled monoclonal antibody directed against human apoB100. The concentration of oxLDL-β₂GPI complex is determined by measuring the enzymatic activity of the HRP using the chromophore reagent tetramethylbenzidine (TMB) which forms a distinct yellow color measured at 450 nm. The intensity of the color produced is measured using a spectrophotometer and is directly proportional to the amount of bound oxLDL-β₂GPI complex. The results are plotted against a standard curve prepared using known solutions of the complex to arrive at the exact measure of circulatory oxLDL-β₂GPI complex in the plasma tested.

A cooking oil of the present invention may be prepared by mixing standard cooking oils with 7.5% w/w algal oil, which contained a minimum of 35% EPA (20%) and DHA (80%) combined. The standard cooking oils selected for the trial are commonly used Groundnut and Sunflower oils. The mixing process is carried out in a closed system under nitrogen (to prevent oxidation) and at temperatures between 20-40 degrees Celsius.

An open labelled randomized study has been carried out to evaluate the effect of this cooking oil on circulatory oxLDL-β₂GPI complex levels in patients with Dyslipidemia in comparison with healthy vegetable cooking oils, namely Groundnut and Sunflower oil.

Patients of either sex were selected aged between 18-60 years with serum LDL cholesterol levels between 130-250 mg/DL and serum triglyceride levels between 150-500 mg/DL. Patients with known coronary artery disease, on dietary therapy for dyslipidemia, on statins/fibrates or other lipid lowering drugs, with severe hepatic disease or renal impairment or pregnant/lactating women, were excluded from the potential pool for this study.

Each patient was subjected to a initial, intermediate (monthly), and final (three months) complete physical examination consisting of measuring RBC with platelets, electrocardiogram, 12 hour fasting lipid profile, fasting blood glucose, thyroid profile, liver function test and renal function test to be able to assess both the efficacy and side effects during the trial period.

Forty eight healthy patients were recruited in approximately equal proportion of males and females and randomly divided, using SAS version 8.2, into three groups A, B and C the treatment was initiated as follows:

Group A—3×500 ml of cooking oil containing 7.5% w/w of algal oil to be used for normal cooking purposes over a period of three months.

Group B 3×500 ml of standard ground nut oil to be used for normal cooking purposes over a period of three months.

Group C—3×500 ml of standard sunflower oil to be used for normal cooking purposes over a period of three months.

In a second trial, forty eight new randomly selected and screened as above patients were divided into two sets, Group A was left untreated and the second set Group B, was given a once a day capsule of commercially available fish oil capsules (2×500 mg) taken every morning with breakfast for 1 month. Circulatory oxLDL-β₂GPI complex levels were measured at day one and day thirty using the same methods as described in the first trial above.

In a third trial, the present inventors compared feeding 24 guinea pigs for 4 weeks a supplemental amount of predominantly a single PUFA and mixed PUFA's, to determine the effectiveness of each in lowering circulatory oxLDL-beta-2 glycoprotein complex, A PUFA combination of 80% DHA, 20% EPA (AO) versus one in which the PUFA concentration is 35% DHA, 35% EPA and 30% DPA (SO) was used and the circulatory oxLDL-β₂GPI was measured using a similar method as described in the first trial above.

In a fourth trial, twenty four new randomly selected and screened human patients were divided into two sets, Group C was left untreated and the second set, Group FO, was given a once a day capsule of commercially available fish oil capsules (2×500 mg) taken every morning with breakfast for 1 month. Circulatory MPO levels were measured at day one and as close to day thirty as possible. Circulatory MPO was accurately measured using an immunometric assay based on a double-antibody 'sandwich' technique (RASA) that detects the circulating MPO in human plasma.

Experimental Results

In the first trial wherein the patients used cooking oil containing 7.5% w/w algal oil versus sunflower and groundnut cooking oils, the plasma was collected and measured for circulatory oxLDL-β₂GPI complex resulting in the results described herein.

The oxLDL-β₂GPI complex concentration curve is first plotted sequentially diluting a reference standard solution, measuring the absorbance (at 450 nm) for each concentration and plotting the calibration curve while simultaneously measuring 24 unknown plasma samples taken in duplicate to measure the unknown concentrations of oxLDL-β₂GPI complex in these samples as shown below in Table 1.

The standard solutions are shown in wells A1-F2 while the patient plasma samples are shown in wells A3-H8 run in duplicates. The number in the patient plasma sample wells denotes the patient numerical code and the letter 1=initial plasma sample, 1M, 2M=1 month or 2 month intermediate plasma samples and F=final plasma sample.

The calibration standard absorbance, results from Table 1 are then plotted in a calibration curve and a second order polynomial equation is extrapolated from the graph.

$$y = 3.6382\beta2 + 89.54x - 0.1227$$

$$R2 = 0.9999$$

TABLE 1

| oxLDL 450 nm | | | | | | | |
|---|---|---|---|---|---|---|---|
| 1 | 2 | 3 | 4 | 5 | 6 | 7 | 8 |
| Std01 | Std01 | 4-I | 4-F | 6-I | 6-F | 7-I | 7-F |
| Std02 | Std02 | 1:1 | 1:1 | 1:1 | 1:1 | 1:1 | 1:1 |
| Std03 | Std03 | 8-I | 8-F | 9-I | 9-F | 10-I | 10-F |
| Std04 | Std04 | 1:1 | 1:1 | 1:1 | 1:1 | 1:1 | 1:1 |
| Std05 | Std05 | 12-I | 12-F | 13-I | 13-F | 14-I | 14-F |
| Std06 | Std06 | 1:1 | 1:1 | 1:1 | 1:1 | 1:1 | 1:1 |
| | | 17-I | 17-F | 18-I | 18-F | 20-I | 20-F |
| | | 1:1 | 1:1 | 1:1 | 1:1 | 1:1 | 1:1 |
| 2.54 | 2.57 | 1.843 | 1.689 | 1.722 | 1.521 | 1.969 | 1.955 |

TABLE 1-continued

| | | | | | | | |
|---|---|---|---|---|---|---|---|
| 1.33 | 1.32 | 1.849 | 1.677 | 1.705 | 1.534 | 1.947 | 1.923 |
| 0.68 | 0.69 | 2.876 | 2.102 | 1.630 | 1.514 | 2.004 | 2.064 |
| 0.34 | 0.35 | 2.899 | 2.130 | 1.609 | 1.523 | 2.018 | 2.057 |
| 0.164 | 0.165 | 1.644 | 1.609 | 1.497 | 1.309 | 1.513 | 1.529 |
| 0.009 | 0.008 | 1.637 | 1.621 | 1.488 | 1.314 | 1.502 | 1.526 |
| | | 1.451 | 1.405 | 2.772 | 2.435 | 2.177 | 2.163 |
| | | 1.421 | 1.399 | 2.778 | 2.441 | 2.175 | 2.164 |

| Calibrator Std | Mean Abs | Dcld Conc U/dl | Obs Conc U/dl |
|---|---|---|---|
| Std01 | 2.555 | 250 | 252.40 |
| Std02 | 1.3250 | 125 | 124.91 |
| Std03 | 0.6850 | 62.5 | 62.92 |
| Std04 | 0.3450 | 31.25 | 31.20 |
| Std05 | 0.1645 | 15.62 | 14.71 |
| Std06 | 0.0085 | 0 | 0.64 |

The equation derived from the calibration curve is applied to the absorbance data from Table 1 to give the corrected concentrations of circulatory oxLDL-$\beta_2$GPI complex in the plasma samples collected from the patients during the course of our study as shown below in Table 2.

TABLE 2

| Corrected Avg Conc (U/dl) | | | | | |
|---|---|---|---|---|---|
| 4-I | 4-F | 6-I | 6-F | 7-I | 7-F |
| 177.566 | 160.878 | 163.986 | 145.139 | 189.145 | 187.175 |
| 8-I | 8-F | 9-I | 9-F | 10-I | 10-F |
| 288.759 | 205.635 | 154.430 | 144.233 | 194.656 | 199.821 |
| 12-I | 12-F | 13-I | 13-F | 14-I | 14-F |
| 156.559 | 153.974 | 141.620 | 123.567 | 143.127 | 145.139 |
| 17-I | 17-F | 18-I | 18-F | 20-I | 20-F |
| 135.960 | 132.564 | 276.367 | 239.801 | 211.943 | 210.627 |

Table 3 below shows a summary of the change in circulatory oxLDL-$\beta_2$GPI complex concentrations over the period of 3 months observed for the 54 patients from our trial. As can be clearly seen, the patients in test Group A who consumed the cooking oil containing the 7.5% w/w algal oil showed a statistically significant lowering in levels of circulatory oxLDL-$\beta_2$GPI complex, which as described earlier should lead to a significant decrease in the development of athero-thrombotic diseases for these patients.

TABLE 3

| Patient ID# | Initials | Sex | Test Oil | Baseline cholesterol | Initial Sample | 1 month sample | % change oxLDL | 2 month sample | % change oxLDL | Final Sample | % change oxLDL |
|---|---|---|---|---|---|---|---|---|---|---|---|
| 3 | A P | M | Group A | 230.50 MG/DL | 01-Nov | 17-Dec | −8.54% | 4-Jan | −9.65% | 04-Feb | −9.43% |
| 4 | S G | F | Group A | 236.50 MG/DL | 01-Nov | 17-Dec | −11.89% | 7-Jan | −11.93% | 05-Feb | −9.40% |
| 5 | P M | F | Group A | 268.90 MG/DL | 01-Nov | 18-Dec | −6.34% | 4-Jan | −9.42% | 04-Feb | −14.82% |
| 6 | J B P | F | Group A | 273.80 MG/DL | 01-Nov | 17-Dec | −5.57% | 4-Jan | −11.66% | 05-Feb | −11.49% |
| 7 | K G | F | Group B | 283.40 MG/DL | 02-Nov | 18-Dec | −1.22% | 7-Jan | −1.87% | 04-Feb | −1.04% |
| 8 | M M | F | Group A | 377.20 MG/DL | 02-Nov | 17-Dec | −12.86% | 8-Jan | −12.42% | 05-Feb | −24.68% |
| 9 | R W | M | Group A | 227.80 MG/DL | 02-Nov | 18-Dec | −20.65% | 8-Jan | −18.65% | 05-Feb | −6.60% |
| 10 | A J | F | Group C | 271.33 MG/DL | 02-Nov | 18-Dec | 1.34% | 8-Jan | 1.21% | 05-Feb | 2.65% |
| 12 | D G | F | Group C | 231.43 MG/DL | 05-Nov | 03-Dec | 2.46% | 8-Jan | 2.85% | 05-Feb | −1.65% |
| 13 | P K | F | Group A | 215.70 MG/DL | 05-Nov | 05-Dec | −8.21% | 10-Jan | −10.02% | 06-Feb | −12.75% |
| 14 | G M | F | Group B | 218.70 MG/DL | 05-Nov | 05-Dec | −1.89% | 10-Jan | −1.57% | 06-Feb | 1.41% |
| 15 | S J | F | Group B | 251.90 MG/DL | 05-Nov | 05-Dec | −2.33% | 10-Jan | −1.81% | 06-Feb | −1.44% |
| 17 | B R | M | Group B | 220.50 MG/DL | 05-Nov | 17-Dec | −1.12% | 10-Jan | −0.93% | 06-Feb | −2.50% |
| 18 | A K | M | Group A | 398.60 MG/DL | 21-Nov | 17-Dec | −10.72% | 15-Jan | −10.90% | 24-Feb | −13.23% |
| 19 | M J | M | Group A | 224.60 MG/DL | 22-Nov | 17-Dec | −9.21% | 29-Jan | −11.39% | 24-Feb | −10.74% |
| 20 | S S K | M | Group B | 258.36 MG/DL | 22-Nov | 21-Dec | 2.79 | 29-Jan | 4.64% | 24-Feb | 2.31 |
| 21 | P N | M | Group A | 222.01 MG/DL | 22-Nov | 21-Dec | −11.39% | 29-Jan | −14.89% | 24-Feb | −8.61% |
| 22 | B P N | F | Group A | 224.71 MG/DL | 22-Nov | 21-Dec | −8.62% | 29-Jan | −10.41% | 24-Feb | −8.34% |
| 23 | B C C | F | Group B | 245.80 MG/DL | 17-Dec | 21-Jan | −1.59% | 15-Feb | −1.33% | 19-Mar | −0.70% |
| 24 | P G K | F | Group B | 269.50 MG/DL | 18-Dec | 14-Jan | 1.94% | 15-Feb | 1.36% | 19-Mar | −2.55% |
| 25 | S P | F | Group B | 275.56 MG/DL | 18-Dec | 14-Jan | 2.54% | 15-Feb | 0.89% | 20-Mar | 2.30% |
| 26 | A R T | M | Group A | 312.00 MG/DL | 17-Dec | 14-Jan | −9.90% | 21-Feb | −11.86% | 20-Mar | −12.21% |
| 27 | P R | M | Group A | 239.15 MG/DL | 20-Dec | 15-Jan | −10.42% | 25-Feb | −10.75% | 20-Mar | −14.67% |
| 28 | B S K | F | Group A | 183.10 MG/DL | 20-Dec | 15-Jan | −7.10% | 25-Feb | −9.82% | 20-Mar | −13.59% |
| 29 | S K | M | Group C | 296.07 MG/DL | 19-Dec | 15-Jan | −0.52% | 25-Feb | 0.95% | 21-Mar | 0.57% |
| 30 | D D | M | Group C | 208.21 MG/DL | 19-Dec | 15-Jan | 0.44% | 26-Feb | 3.46% | 21-Mar | 2.93 |
| 31 | V R P | F | Group A | 153.45 MG/DL | 19-Dec | 15-Jan | −6.45% | 27-Feb | −2.96% | 21-Mar | −6.48% |
| 32 | R D | F | Group A | 228.87 MG/DL | 19-Dec | 14-Jan | −8.63% | 26-Feb | −9.42% | 21-Mar | −16.72% |
| 33 | M G | F | Group A | 262.61 MG/DL | 20-Dec | 15-Jan | −14.65% | 26-Feb | −5.84% | 25-Mar | −11.05% |
| 34 | F A | M | Group C | 242.60 MG/DL | 20-Dec | 21-Jan | 2.56% | 27-Feb | 2.14% | 25-Mar | 1.94% |
| 35 | M S S | F | Group C | 259.54 MG/DL | 21-Dec | 21-Jan | 3.85% | 27-Feb | −0.58% | 25-Mar | −0.97% |
| 37 | A K | M | Group C | 250.70 MG/DL | 20-Dec | 21-Jan | 0.55% | 27-Feb | −0.52% | 25-Mar | −0.41% |
| 38 | S K S | M | Group C | 248.74 MG/DL | 21-Dec | 21-Jan | 0.33% | 26-Feb | −0.09% | 25-Mar | 1.45% |
| 39 | R S W | M | Group C | 209.90 MG/DL | 17-Jan | 21-Feb | 1.26% | 20-Mar | −2.01% | 20-Apr | −2.39% |
| 40 | R J | F | Group C | 295.00 MG/DL | 17-Jan | 21-Feb | 1.94% | 20-Mar | 0.87% | 20-Apr | 1.60% |
| 41 | A L | M | Group A | 268.00 MG/DL | 18-Jan | 21-Feb | −8.75% | 21-Mar | −4.64% | 20-Apr | −6.52% |
| 42 | M R G | F | Group B | 211.40 MG/DL | 17-Jan | 22-Feb | −2.45% | 20-Mar | −2.13% | 20-Apr | −1.71% |
| 43 | M S K | M | Group A | 180.68 MG/DL | 17-Jan | 29-Feb | −5.65% | 20-Mar | −6.47% | 20-Apr | −9.72% |
| 44 | A K | M | Group A | 202.10 MG/DL | 18-Jan | 29-Feb | −6.71% | 21-Mar | −11.05% | 22-Apr | −11.29% |
| 45 | S V | F | Group B | 150.80 MG/DL | 18-Jan | 29-Feb | −1.32% | 21-Mar | −1.78% | 22-Apr | −1.48% |
| 46 | J L | M | Group A | 280.40 MG/DL | 18-Jan | 29-Feb | −9.59% | 21-Mar | −7.34% | 22-Apr | −12.26% |
| 47 | C S | F | Group A | 243.90 MG/DL | 01-Feb | 06-Mar | −4.45% | 4-Apr | −6.58% | 05-May | −8.83% |
| 48 | P G T | F | Group B | 221.4 MG/DL | 04-Mar | 07-Apr | −0.84% | 5-May | −2.67% | 11-Jun | −1.22% |

TABLE 3-continued

| Patient ID# | Initials | Sex | Test Oil | Baseline cholesterol | Initial Sample | 1 month sample | % change oxLDL | 2 month sample | % change oxLDL | Final Sample | % change oxLDL |
|---|---|---|---|---|---|---|---|---|---|---|---|
| 49 | S S D | M | Group C | 210.4 MG/DL | 04-Mar | 07-Apr | 1.79% | 6-May | 3.16% | 11-Jun | 3.86% |
| 50 | U S P | M | Group C | 199.7 MG/DL | 04-Mar | 07-Apr | 2.03% | 6-May | 2.70% | 11-Jun | 2.01% |
| 51 | S S N | M | Group A | 312.88 MG/DL | 06-Mar | 07-Apr | −5.33% | 14-May | −8.01% | 12-Jun | −11.47% |
| 52 | S S G | M | Group A | 284.5 MG/DL | 06-Mar | 17-Apr | −13.58% | 14-May | −11.04% | 12-Jun | −17.73% |
| 53 | A P C | M | Group C | 271 MG/DL | 07-Mar | 18-Apr | −1.47% | 14-May | −1.42% | 12-Jun | −1.27% |

The mean reduction circulatory oxLDL-$\beta_2$GPI complex in the test Group A is −11.78% which is significantly greater than the mean reduction from control Group B at −0.33% and the numerical increase in circulatory oxLDL-$\beta_2$GPI complex seen from control Group C at 0.64%. Statistical significance is seen with standard deviations of 0.016, 0.011 and 0.011 and a confidence level of 0.021, 0.010, 0.010 at an alpha of 0.01 for the three groups respectively.

In the second trial, patients were given a 2×500 mg capsules of fish oil once a day and circulatory oxLDL-$\beta_2$GPI complex levels were measured in the manner described above, at the start and at the end of the thirty days and the results are shown herein.

The fish oil was analyzed for its lipid profile which is shown below in Table 4 and shows the presence of mixed PUFA's (EPA, DPA, DHA) and the results of the measurement of circulatory oxLDL-$\beta_2$GPI complex is shown below in Table 5.

TABLE 4

| | | |
|---|---|---|
| FFA | | 1.3% |
| Peroxide Value | | 3.4 ppm |
| Fatty Acid | | Wt % |
| 16:0 | | 0.6 |
| 18:0 | | 1.0 |
| 18:1 | | 1.8 |
| 18:2 | | 0.4 |
| 20:0 | | 2.3 |
| 20:1 | | 1.5 |
| 20:2 | | 0.4 |
| 20:3 | | 3.3 |
| 20:4 | | 1.2 |
| 20:5 (EPA) | | 17.8 |
| 22:0 | | 2.7 |
| 22:1 | | 0.6 |
| 22:2 | | 1.8 |
| 22:3 | | 2.0 |
| 22:5 (DPA) | | 7.1 |
| 22:6 (DHA) | | 51.9 |
| 24:0 | | 1.8 |
| 24:1 | | 1.8 |

The mean reduction in circulatory oxLDL-$\beta_2$GPI complex in the test Group F (fish oil capsule) is −9.77% which is significantly different from the numerical increase in circulatory oxLDL-$\beta_2$GPI complex seen from control group labeled "C" at 0.54% as shown below in Table 5. Statistical significance is seen with standard deviations of 0.014, 0.005 with a confidence level of 0.007 and 0.002 at an alpha of 0.05 for the F and C groups respectively.

TABLE 5

| Patient ID# | Test Oil | Initial Sample | 1 month sample | % change oxLDL |
|---|---|---|---|---|
| 1 | C | 26-Mar | 08-May | 0.69% |
| 2 | F | 26-Mar | 07-May | −11.61% |
| 3 | F | 26-Mar | 05-May | −8.99% |

TABLE 5-continued

| Patient ID# | Test Oil | Initial Sample | 1 month sample | % change oxLDL |
|---|---|---|---|---|
| 4 | F | 26-Mar | 14-May | −9.92% |
| 5 | C | 26-Mar | 08-May | 0.34% |
| 6 | C | 28-Mar | 05-May | 0.77% |
| 7 | C | 28-Mar | 05-May | 0.39% |
| 8 | F | 28-Mar | 08-May | −9.71% |
| 9 | C | 28-Mar | 08-May | 0.43% |
| 10 | F | 28-Mar | 08-May | −8.09% |
| 11 | C | 28-Mar | 14-May | 1.07% |
| 12 | F | 29-Mar | 06-May | −9.39% |
| 13 | C | 29-Mar | 06-May | 1.17% |
| 14 | C | 29-Mar | 06-May | 0.32% |
| 15 | F | 29-Mar | 06-May | −9.41% |
| 16 | F | 29-Mar | 06-May | −10.26% |
| 17 | F | 29-Mar | 06-May | −12.73% |
| 18 | C | 31-Mar | 08-May | 0.28% |
| 19 | C | 31-Mar | 05-May | 0.89% |
| 20 | C | 31-Mar | 08-May | 1.14% |
| 21 | C | 01-Apr | 08-May | −0.22% |
| 22 | C | 01-Apr | 14-May | 0.71% |
| 23 | F | 01-Apr | 08-May | −9.35% |
| 24 | F | 01-Apr | 05-May | −10.73% |
| 25 | C | 26-Mar | 08-May | 0.69% |
| 26 | C | 26-Mar | 07-May | 0.61% |
| 27 | F | 26-Mar | 05-May | −8.99% |
| 28 | C | 26-Mar | 14-May | 0.92% |
| 29 | C | 26-Mar | 08-May | −0.34% |
| 30 | C | 28-Mar | 05-May | 0.77% |
| 31 | C | 28-Mar | 05-May | −0.27% |
| 32 | F | 28-Mar | 08-May | −9.38% |
| 33 | C | 28-Mar | 08-May | 0.52% |
| 34 | F | 28-Mar | 08-May | −10.07% |
| 35 | C | 28-Mar | 14-May | 0.77% |
| 36 | F | 29-Mar | 06-May | −9.39% |
| 37 | C | 29-Mar | 06-May | −0.39% |
| 38 | C | 29-Mar | 06-May | 0.75% |
| 39 | F | 29-Mar | 06-May | −7.41% |
| 40 | F | 29-Mar | 06-May | −11.69% |
| 41 | F | 29-Mar | 06-May | −12.73% |
| 42 | F | 31-Mar | 08-May | −8.28% |
| 43 | F | 31-Mar | 05-May | −9.22% |
| 44 | C | 31-Mar | 08-May | 0.86% |
| 45 | F | 01-Apr | 08-May | −8.33% |
| 46 | F | 01-Apr | 14-May | −8.73% |
| 47 | F | 01-Apr | 08-May | −9.35% |
| 48 | F | 01-Apr | 05-May | −10.73% |

In a further-experiment with guinea pigs, we compared feeding 24 guinea pigs for 4 weeks a supplemental (250 mg/1 kg body wt) amount of algal oil (AO) was compared to a supplemental (250 mg/1 kg body wt) salmon oil (SO), to determine the effectiveness of each oil in lowering circulatory oxLDL-beta2 glycoprotein complex. A PUFA combination of 80% DHA, 20% EPA (AO) versus one in which the PUVA concentration is 35% DHA, 35% EPA and 30% DPA (SO) was used. We found both lowered oxLDL complex but mixed PUFA's were approx 3-fold more effective. The results of the experiment are shown in Table 6. The energy distribution of the diets was 45:30:25 carbohydrate:fat:protein.

TABLE 6

| Guinea Pig ID# | Sex | Test Oil | Baseline cholesterol mg/dL | Plasma oxLDL Initial Sample mg/dL | Plasma oxLDL Final Sample mg/dL | % change oxLDL |
|---|---|---|---|---|---|---|
| 1 | F | Group A | 80.4 | 31.6 | 27.3 | −13.61% |
| 2 | M | Group B | 79.8 | 33.2 | 31.6 | −4.82% |
| 3 | F | Group A | 76.4 | 29.8 | 27.0 | −9.40% |
| 4 | F | Group B | 80.3 | 31.8 | 30.1 | −5.35% |
| 5 | M | Group A | 83.2 | 28.5 | 24.8 | −12.98% |
| 6 | M | Group B | 82.6 | 30.7 | 29.4 | −4.23% |
| 7 | F | Group A | 77.9 | 34.2 | 30.4 | −11.11% |
| 8 | M | Group B | 78.2 | 27.4 | 25.7 | −6.20% |
| 9 | F | Group A | 83.1 | 29.6 | 25.8 | −12.84% |
| 10 | M | Group B | 82.7 | 30.1 | 28.6 | −4.98% |
| 11 | F | Group A | 81.4 | 30.5 | 27.2 | −10.82% |
| 12 | M | Group B | 77.7 | 29.7 | 28.4 | −4.38% |
| 13 | F | Group A | 79 | 31.6 | 28.1 | −11.08% |
| 14 | M | Group B | 80.6 | 29.4 | 28.0 | −4.76% |
| 15 | M | Group A | 81.3 | 30.8 | 26.5 | −13.96% |
| 16 | F | Group B | 79.8 | 32.4 | 31.1 | −4.01% |
| 17 | F | Group A | 78.6 | 31.9 | 27.8 | −12.85% |
| 18 | M | Group B | 79.2 | 31.7 | 30.7 | −3.15% |
| 19 | M | Group A | 81.5 | 31.9 | 28.0 | −12.23% |
| 20 | F | Group B | 82.4 | 30.0 | 28.7 | −4.33% |
| 21 | F | Group A | 82.1 | 30.8 | 27.3 | −11.36% |
| 22 | F | Group B | 81.3 | 28.8 | 27.5 | −4.51% |
| 23 | M | Group A | 80.7 | 29.2 | 25.7 | −11.99% |
| 24 | M | Group B | 79.2 | 32.1 | 30.5 | −4.98% |

Group A was fed 250 mg/kg body wt of Salmon Oil
Group B was fed 250 mg/kg body wt of Algal Oil
Average Reduction in circulatory oxLDL in Group A=−12.02%+/−0.71 at 95% confidence level
Average Reduction in circulatory oxLDL in Group B=−4.64%+/−0.40 at 95% confidence level Analysis of the Effect on Circulatory MPO During the course of our research in lowering of oxidized-LDL-beta-2-glycoproteins in subjects prescribed 2×500 mg fish oil capsules per day containing mixed PUFA's, we also investigated one of the mechanisms by which such a lowering of oxLDL might be occurring, namely a commensurate reduction in circulatory myleoperoxidase.

An open labelled randomized study was carried out to evaluate the effect of this cooking oil on circulatory oxLDL-$\beta_2$GPI complex levels in patients with Dyslipidemia in comparison with healthy vegetable cooking oils, namely Groundnut and Sunflower oil.

Twenty four healthy patients of either sex aged between 20-50 years and who were self-declared as being healthy for 15 days prior to recruitment were recruited in approximately equal proportion of males and females and randomly divided, using SAS version 8.2, into two groups C (Control Untreated) and F (Fish Oil Capsule Treated). Patients with known coronary artery disease, on dietary therapy for dyslipidemia, on statins/fibrates or other lipid lowering drugs, with severe hepatic disease or renal impairment or pregnant/lactating women, were excluded from the potential pool for this study. Each patient was subjected to a initial screening physical examination to ensure the good health of each subject.

Each patient in group F was given a 2×500 mg capsule of fish oil for swallowing once a day during breakfast. Blood was drawn on the first and approximately 30$^{th}$ day of treatment and circulatory MPO levels were measured in the plasma.

The mean reduction in circulatory MPO was measured by a modified ELISA assay at 405 nm. Test Group F (fish oil capsule) showed a statistically significantly greater reduction at −8.1% as compared to the numerical decrease in circulatory MPO seen from control group labeled. "C" at −0.3% as shown below in Table 7. Statistical significance is seen with standard deviations of 0.011, 0.006 with a confidence level of 0.006 and 0.003 at an alpha of 0.05 for the F and C groups respectively.

TABLE 7

Change in circulatory levels of MPO (2 × 500 mg FO capsule for 1 month)

| Patient ID# | Test Oil | Initial Sample | 1 month sample | % change MPO |
|---|---|---|---|---|
| 1 | C | 26-Mar | 08-May | 0.8% |
| 2 | F | 26-Mar | 07-May | −6.7% |
| 3 | F | 26-Mar | 05-May | −9.4% |
| 4 | F | 26-Mar | 14-May | −7.2% |
| 5 | C | 26-Mar | 08-May | −0.4% |
| 6 | C | 28-Mar | 05-May | 0.5% |
| 7 | C | 28-Mar | 05-May | −0.4% |
| 8 | F | 28-Mar | 08-May | −8.6% |
| 9 | C | 28-Mar | 08-May | −0.9% |
| 10 | F | 28-Mar | 08-May | −6.3% |
| 11 | C | 28-Mar | 14-May | −0.6% |
| 12 | F | 29-Mar | 06-May | −7.9% |
| 13 | C | 29-Mar | 06-May | −0.2% |
| 14 | C | 29-Mar | 06-May | 0.0% |
| 15 | F | 29-Mar | 06-May | −9.1% |
| 16 | F | 29-Mar | 06-May | −9.7% |
| 17 | F | 29-Mar | 06-May | −8.4% |
| 18 | C | 31-Mar | 08-May | −0.4% |
| 20 | C | 31-Mar | 08-May | 0.3% |
| 21 | C | 01-Apr | 08-May | −0.8% |
| 22 | C | 01-Apr | 14-May | −0.9% |
| 23 | F | 01-Apr | 08-May | −8.9% |
| 24 | F | 01-Apr | 05-May | −7.6% |
| 25 | F | 26-Mar | 08-May | −7.8% |

| | Mean Reduction | SD | 95% Confidence |
|---|---|---|---|
| F - Fish Oil | −8.1% | 0.011 | 0.0061 |
| C = Control | −0.3% | 0.006 | 0.0031 |

Embodiments of the invention are methods to reduce circulating oxLDL-beta-2-glycoprotein 1 complex and circulating MPO levels in human sera as a means of prevention and treatment of atherosclerosis comprising administering to a person an effective amount of a dietary oil composition containing 1-99 wt % polyunsaturated fatty acids (PUFA).

Embodiments of the invention further comprise methods wherein the dietary oil composition further comprises an edible cooking oil, where the composition comprises a fatty acid distribution of saturated fatty acids (SFA) 15-55 wt %; mono unsaturated fatty acids (MUFA) 40-80 wt %; and polyunsaturated fatty acids (PUFA) 5-45 wt %.

Embodiments of the invention further comprise methods wherein the dietary oil composition is administered via a capsule, the capsule containing a dietary oil composition comprising a fatty acid distribution of saturated fatty acids (SFA) 5-10 wt %; mono unsaturated fatty acids (MUFA) 5-10 wt %; and polyunsaturated fatty acids (PUFA) 20-90 wt %.

Embodiments of the invention further comprise methods wherein the preferred polyunsaturated fatty acids are Eicosa Pentaenoic Acid (EPA), Docosa Pentaenoic Acid (DPA) and Docosa Hexaenoic Acid (DHA), preferably in a ration of 0.1-1, 0.1-0.5, and 0.5-1.

Embodiments of the invention further comprise methods wherein the PUFA fraction comprises at least one oil selected from the group consisting of marine oil and algal oil, wherein the marine oil and algal oil comprise EPA, DHA, DPA and natural anti-oxidants.

Embodiments of the invention further comprise methods wherein the edible cooking oil comprises vegetable oil.

Embodiments of the invention further comprise methods wherein the edible cooking oil comprises an oil selected from the group consisting of groundnut oil, rice-bran oil, soybean oil, corn oil, sesame oil, canola oil, safflower oil, olive oil, and peanut oil.

Embodiments of the invention further comprise methods wherein the edible cooking oil further comprises at least one of Vitamin A, Vitamin D, Vitamin E, or an anti-oxidant plant extract.

Embodiments of the invention further comprise a process for the manufacture of a dietary oil composition comprising:
 a) charging a vessel with an edible cooking oil;
 b) adding at least one oil selected from the group consisting of marine oil and algal oil to the vessel; and
 c) stirring the oils until blended.

I claim:

1. A method to reduce circulating oxLDL-beta-2-glycoprotein 1 complex in human sera comprising:
   administering to a person an effective amount of a dietary oil composition comprising mixture of 15-55 wt. % saturated fatty acids, 40-80 wt. % mono-unsaturated fatty acids, and 5-45 wt. % polyunsaturated fatty acids wherein the polyunsaturated fatty acids (PUFAs) Docsa Hexenoic acid (DHA), Eicosa Pentenoic Acid (EPA) and Docosa Pentenoic Acid (DPA) in a concentration ratio of about 35% DHA, about 35% EPA, and about 30% DPA.

2. The method of claim 1 wherein the dietary oil composition further comprises an edible cooking oil;
   wherein the combination of PUFAs is provided as a combination of Docosa Hexenoic Acid (DHA), Eicosa Pen enoic acid (EPA) and Docosa Pentenoic acid (DPA) such that the combination is substantially free of any single predominant PUFA.

3. The method of claim 1 whet the dietary oil composition is administered via a capsule, the capsule containing a dietary oil composition comprising fatty acid distribution of:
   (i) saturated fatty acids (SFA) 15-55 wt %;
   (ii) mono unsaturated fatty acids (MUFA) 40-80 wt %; and
   (iii) polyunsaturated fatty acids (PUFA) 5-45 wt %.

4. A method as in claim 1 wherein the edible cooking oil comprises vegetable oil.

5. A method as in claim 1 wherein the edible cooking oil comprises an oil selected from the group consisting of groundnut oil, rice-bran oil, soybean oil, corn oil, sesame oil, canola oil, safflower oil, olive oil, and peanut oil.

6. A method as in claim 1 wherein the source of polyunsaturated fatty acids is salmon oil.

7. A method as in claim 1 wherein the composition is effective at a human dose of 1000 mg per day.

* * * * *